United States Patent [19]

Hubele

[11] 4,093,738
[45] June 6, 1978

[54] MICROBICIDALLY-ACTIVE ACYLATED ANILINO-CARBOXYLIC ACID ESTERS AND THEIR COMPOSITIONS

[75] Inventor: Adolf Hubele, Magden, Switzerland

[73] Assignee: Ciba-Geigy Corporation, Ardsley, N.Y.

[21] Appl. No.: 723,825

[22] Filed: Sep. 16, 1976

Related U.S. Application Data

[63] Continuation-in-part of Ser. No. 564,016, Apr. 1, 1975, abandoned.

[30] Foreign Application Priority Data

Apr. 9, 1974 Switzerland .................. 4998/74
Mar. 7, 1975 Switzerland .................. 2906/75

[51] Int. Cl.$^2$ ............... A61K 31/24; C07C 101/18
[52] U.S. Cl. .................. 424/309; 260/518 A; 260/518 R; 260/454; 260/465 D; 424/304; 424/324; 424/319; 424/302; 560/43
[58] Field of Search .............. 260/471 A; 424/309

[56] References Cited

U.S. PATENT DOCUMENTS

| | | | |
|---|---|---|---|
| 3,598,859 | 8/1971 | Yates et al. | 260/471 |
| 3,780,095 | 12/1973 | Klemm et al. | 260/518 A |
| 3,994,713 | 11/1976 | Hadclock | 71/111 |
| 4,025,648 | 5/1977 | Hubele | 424/309 |

FOREIGN PATENT DOCUMENTS 730,316  1/1973  South Africa.

*Primary Examiner*—Donald G. Daus
*Assistant Examiner*—Lisa Jones
*Attorney, Agent, or Firm*—Harry Falber

[57] ABSTRACT

Microbicidally active compounds of the formula I

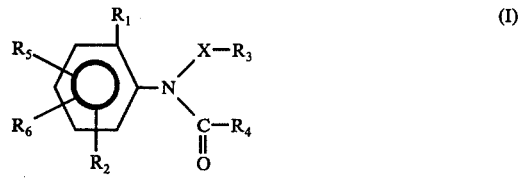

wherein $R_1$ represents alkyl of 1 to 4 carbon atoms, alkoxy of 1 to 4 carbon atoms or halogen, $R_2$ represents hydrogen, alkyl of 1 to 3 carbon atoms, alkoxy of 1 to 4 carbon atoms or halogen, $R_5$ represents hydrogen, alkyl of 1 to 3 carbon atoms or halogen, $R_6$ represents hydrogen or methyl, the total number of carbon atoms of the substituents $R_1$, $R_2$, $R_5$ and $R_6$ in the phenyl ring not exceeding 8, X represents —CH$_2$— or

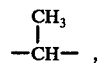

$R'_3$ represents —COOR' or

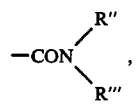

wherein each of R', R" and R'" independently represents hydrogen, methyl, or ethyl, and $R_4$ represents alkyl of 1 to 6 carbon atoms, which is unsubstituted or substituted by cyano (-CN) or rhodano (—SCN), alkenyl of 2 to 5 carbon atoms or cycloalkyl of 3 to 7 carbon atoms.

16 Claims, No Drawings

MICROBICIDALLY-ACTIVE ACYLATED ANILINO-CARBOXYLIC ACID ESTERS AND THEIR COMPOSITIONS

CROSS-REFERENCE

This application is a continuation-in-part of our application Ser. No. 564,016, filed Apr. 1, 1975, now abandoned.

The present invention provides compounds of the formula I

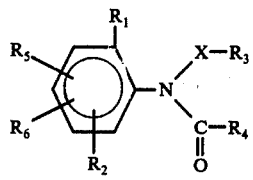

wherein $R_1$ represents alkyl of 1 to 4 carbon atoms, alkoxy of 1 to 4 carbon atoms or halogen, $R_2$ represents hydrogen, alkyl of 1 to 3 carbon atoms, alkoxy of 1 to 4 carbon atoms or halogen, $R_5$ represents hydrogen, alkyl of 1 to 3 carbon atoms or halogen, $R_6$ represents hydrogen or methyl, the total number of carbon atoms of the substituents $R_1$, $R_2$, $R_5$ and $R_6$ in the phenyl ring not exceeding 8, X represents —$CH_2$— or

$R_3$ represents —COOR' or

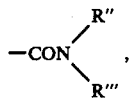

wherein each of R', R" and R'" independently represents hydrogen, methyl, or ethyl, and $R_4$ represents alkyl of 1 to 6 carbon atoms, which is unsubstituted or substituted by cyano (—CN) or rhodano (—SCN), alkenyl of 2 to 5 carbon atoms or cycloalkyl of 3 to 7 carbon atoms as active substances for combatting microorganisms.

The invention further provides compounds of the formula Ia

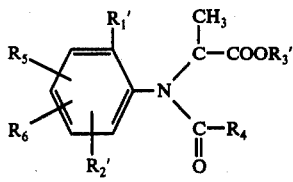

wherein
$R'_1$ represents methyl
$R'_2$ represents methyl, ethyl or chlorine
$R_5$ represents hydrogen, alkyl of 1 to 3 carbon atoms or halogen and
$R_6$ represents hydrogen or methyl; the total number of carbon atoms in $R_1$, $R_2$, $R_5$, $R_6$ not exceeding 8;
$R_3$ represents hydrogen, methyl or ethyl and
$R_4$ represents alkyl of 1 to 6 carbon atoms optionally substituted by cyano or rhodano, alkenyl of 2 to 5 carbon atoms or cycloalkyl of 3 to 7 carbon atoms as well as microbicidal compositions containing them as active substances.

By alkyl and as alkyl moiety of an alkoxy group are meant the following groups, depending on the number of the indicated carbon atoms: methyl, ethyl, n-propyl, isopropyl, n-butyl, isobutyl, sec. or tert. butyl as well as the pentyl or hexyl isomers. Examples of alkenyl radicals are vinyl, allyl, methallyl, butenyl, methylbutenyl and their isomers, while the cycloalkyl radicals comprise cyclopropyl, cyclobutyl, cyclopentyl, cyclohexyl and cycloheptyl. Halogen is fluorine, chlorine, bromine or iodine.

German Offenlegungsschrift No. 2,212,268 discloses in general terms that N-haloacylated anilinoalkanecarboxylic esters possess selective herbicidal action. However, only a number of N-haloacylated 2,6-dialkylanilinoacetic acids and esters thereof are mentioned by name and shown to be herbicides. No references as to microbicidal, especially plant fungicidal, action are provided.

U.S. Pat. No. 3,598,859 generically discloses the compounds of the formula I without specifically mentioning any compounds falling within the scope thereof. There is no mention made of microbicidal activity.

The present invention is based on the surprising observation that the compounds of the formula I and particularly those of the formula Ia exhibit a very favourable microbicidal spectrum for practical use in plant protection. Previously disclosed similar compounds have not shown such activity.

Examples of plants to be protected are:
cereals, maize, rice, vegetables, sugar-beet, soya, ground nuts, fruit trees, ornamental plants, but principally vines, hops, cucumber plants (cucumber, marrows, melons) and solanaceae, such as potatoes, tobacco and tomatoes, as well as banana, cocoa and rubber plants.

With the active substances of the formula I it is possible to destroy the fungi which attack plants or parts of plants (fruit, blossoms, leaves, stems, tubers, roots) and also to protect parts of plants which grow later. The active substances act against the phytopathogenic fungi which belong to the following classes: ascomycetes (erysiphaceae); basidiomycetes, above all rust fungi; fungi imperfecti (moniliales) such as cercospora; but especially against the oomycetes which belong to the class of the phycomycetes, e.g. phytophthora, peronospora, pseudoperonospora, pythium or plasmopara. In addition, the compounds of the formula I have a systemic action. They can also be used as seed-dressing agents for protecting seeds (fruit, tubers, kernels) and plant cuttings from fungus infections as well as from phytopathogenic fungi which occur in the soil.

Preferred compounds of the formula I are those of the formula Ia as defined above.

Compounds of the formula Ia to be singled out for special mention on account of their activity are those wherein
$R'_3$ represents methyl
$R_4$ represents alkyl or alkenyl of 2 to 4 carbon atoms or cycloalkyl of 3 to 4 carbon atoms and the total number of carbon atoms in $R_1$, $R_2$, $R_5$ and $R_6$ does not exceed 4.

Another important subgroup of compounds comprises those of the formula Ia wherein
$R'_2$ represents methyl
$R_5$ represents hydrogen, methyl, chlorine or bromine, $R_6$ represents hydrogen and
$R_4$ represents vinyl, allyl, n-propyl or cyclopropyl.

A further group of preferred compounds are those of the formula Ia wherein
$R'_2$ represents chlorine or ethyl
$R_5$ and $R_6$ represent hydrogen
$R'_3$ represents methyl and
$R_4$ represents vinyl, allyl, n-propyl or cyclopropyl.

Particularly preferred individual compounds are N-(1'-methoxycarbonyl-ethyl)-N-crotonoyl-3-bromo-2,6-dimethylaniline of the formula

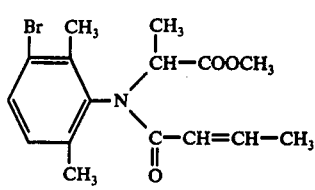

N-(1'-methoxycarbonyl)-N-n-butyryl-2,3,6-trimethylaniline of the formula

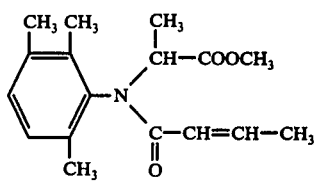

N-(1'-methoxycarbonyl)-N-cyclopropanoyl-2,3,6-trimethylaniline of the formula

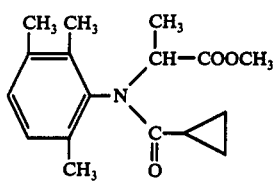

and N-(1'-methoxycarbonyl-ethyl)-N-cyclopropanoyl-2-methyl-4-sec. butoxy-aniline of the formula

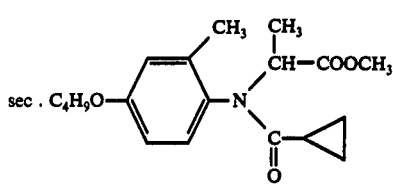

The compounds of the formula I are manufactured by acylation of a compound of the formula II

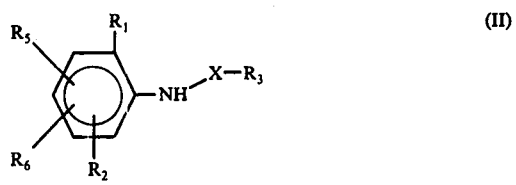

with a carboxylic acid of the formula III

or with the acid halide, acid anhydride or ester thereof, in isolated instances also with one of the acid amides thereof (transamidation).

It is also possible to manufacture the compounds of the formula I by converting the acyl anilide of the formula IV

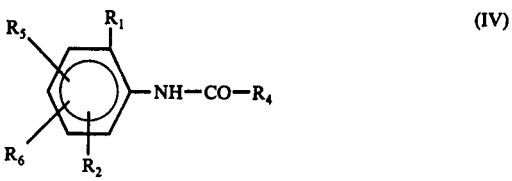

with butyl lithium or sodium hydride into the corresponding alkali salt, which is then reacted with a compound of the formula V

to give the desired end product, or else to react the acyl anilide of the formula IV with the compound of the formula V in the presence of an alkali carbonate (e.g. $Na_2CO_3$ or $K_2CO_3$) as proton acceptor, preferably with the addition of catalytic amounts of alkali iodide (e.g. potassium iodide).

In the formulae II, III, IV and V, the symbols $R_1$ to $R_6$ and X have the meanings assigned to them in formula I and Hal represents a halogen atom, preferably chlorine or bromine or another easily removable radical. The term "acid halide" denotes preferably the acid chloride or acid bromide. The reactions can be carried out in the presence or absence of solvents or diluents which are inert to the reactants. Examples of suitable solvents or diluents are: aliphatic or aromatic hydrocarbons, e.g. benzene, toluene, xylene, petroleum ether; halogenated hydrocarbons, e.g. chlorobenzene, methylene chloride, ethylene chloride, chloroform; ethers and ethereal compounds, e.g. dialkyl ethers, dioxan, tetrahydrofuran; nitriles, e.g. acetonitrile; N,N-dialkylated amides, e.g. dimethyl formamide; dimethyl sulphoxide, ketones, e.g. methyl ethyl ketone, and mixtures of such solvents.

The reaction temperatures are between 0° and 180° C, preferably between 20° C and 120° C. It is often advantageous to use acid acceptors or condensation agents. Suitable examples are: tertiary amines, e.g. trialkylamines (e.g. triethylamines), pyridine and pyridine bases, or inorganic bases, e.g. the oxides and hydroxides, hydrogen carbonates and carbonates of alkali metals and alkaline earth metals, as well as sodium acetate. Moreover, in the first manufacturing method, it is also possible to use a surplus of the respective aniline derivative of the formula II as acid acceptor.

The process of manufacture which proceeds from compounds of the formula II can also be carried out without acid acceptors; in some instances it is expedient to pass in nitrogen in order to expel the hydrogen halide that has formed. In other instances it is very advantageous to use dimethyl formamide as reaction catalyst.

Particulars on the manufacture of the intermediates of the formula II can be inferred from the methods which are generally indicated for the manufacture of aniline-alkane acid esters in the following publications:
J.Org. Chem. 30, 4101 (1965); Tetrahedron 1967, 487; Tetrahedron 1967, 493.

The compounds of the formula I in which

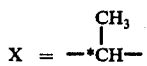

$$X = -*CH-\overset{CH_3}{|}$$

contain and asymmetrical carbon atom (*) and can be resolved into the optical antipodes in the customary manner. In this connection, the enantiomeric D-form has the more pronounced microbicidal action.

Within the scope of the invention, those compounds, their compositions and their use which refer to the D-configurations of the formula I are accordingly preferred.

The pure optical antipodes may be obtained by known methods for example by preparing salts of the starting material of the formula (VI)

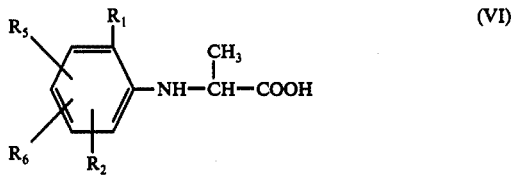

with an optically active base such as a nitrogen containing base, eg. α-phenylethylamine, and isolating the pure anitpode by fractional crystallisation followed by liberation of the optically active free acid. Optically active starting materials of the formula II can then be prepared from this acid.

Independently of this optical isomerism, an atropisomerism is observed about the phenyl—N< axis in those instances in which the phenyl ring is substituted at least in 2,6-position and at the same time unsymmetrically to the axis (i.e. also on account of the presence of additional substituents as the case may be).

Also irrespective of the optical isomerism, where $R_4$ is alkenyl a cis/trans-isomerism can occur in the double bond.

Provided no synthesis with the object of isolating pure isomers is carried out, a product will normally occur as a mixture of the possible isomers.

The following Examples will serve to illustrate the invention in more detail but do not limit it. Unless stated to the contrary, reference to an active substance of the formula I, which can occur in optionally active form, is always to be understood as meaning the racemic mixture.

EXAMPLE 1

Manufacture of

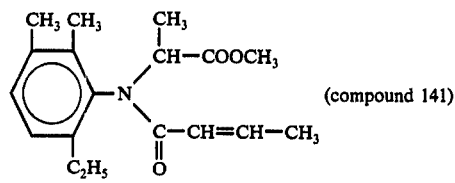

(compound 141)

N-(1'-methoxycarbonyl-ethyl)-N-crotonoyl-2,3-dimethyl-6-ethylaniline.

(a) A mixture of 100 g of 2,3-dimethyl-6-ethylaniline, 223 g of 2-bromopropionic acid methyl ester and 84 g of $NaHCO_3$ was stirred for 17 hours at 140° C, then cooled, diluted with 300 ml of water and extracted with diethyl ether. The extract was washed with a small amount of water, dried over sodium sulphate, filtered and the ether was evaporated. After the excess 2-bromopropionic acid methyl ester has been distilled off, the crude product was distilled in a high vacuum; b.p. 88°–90° C/0.04 Torr.

(b) A mixture of 17 g of the ester obtained according to (a), 10.4 g of crotonic chloride, 2 ml of dimethyl formamide and 150 ml of abs. toluene was refluxed for 1 hour. The solvent was evaporated off and the crude product then distilled in vacuo; b/p. 128°–129° C/0.03 Torr.

The D-forms of both cis/trans-isomers (compounds 141 a and 141 b) are obtained by acylating the pure D-form of α-(2,3-dimethyl-6-ethylanilino)-propionic acid methyl ester with crotonic acid or with one of the reactive derivatives thereof.

The other intermediates may also be manufactured in a manner analogous to that of Example 1(a), including e.g. the following compounds of the formula IIa ($R_1$ = 2-position):

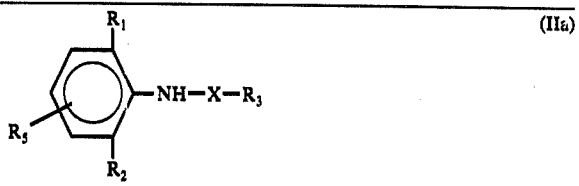

| $R_1$ | $R_2$ | $R_5$ | $-X-R_3$ | Physical constant (temperatures in °C) |
|---|---|---|---|---|
| $CH_3$ | $CH_3$ | H | $-CH(CH_3)-COOCH_3$ | b.p. 98°/0.8Torr |

-continued

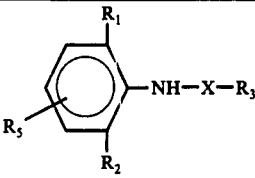

(IIa)

| $R_1$ | $R_2$ | $R_5$ | $-X-R_3$ | Physical constant (temperatures in ° C) |
|---|---|---|---|---|
| $CH_3$ | $C_2H_5$ | H | $-CH(CH_3)-COOCH_3$ | b.p. 88 – 90°/0.01Torr |
| $CH_3$ | $C_2H_5$ | 5-$CH_3$ | $-CH(CH_3)-COOCH_3$ | b.p. 96 – 99°/0.03Torr |
| $CH_3$ | $CH_3$ | 3-$CH_3$ | $-CH(CH_3)-COOCH_3$ | b.p. 83°/0.03Torr; 145°/9Torr |
| $CH_3$ | $CH_3$ | 4-$CH_3$ | $-CH(CH_3)-COOCH_3$ | b.p. 88 – 90°/0.04Torr |
| $CH_3$ | $C_2H_5$ | 3-$CH_3$ | $-CH(CH_3)-COOCH_3$ | b.p. 88 – 90°/0.04Torr |
| $CH_3$ | H | 4-$CH_3$ | $-CH(CH_3)-COOCH_3$ | b.p. 95 – 100°/0.02Torr |
| $CH_3$ | H | 5-$CH_3$ | $-CH(CH_3)-COOCH_3$ | b.p. 106 – 108°/0.1Torr |
| $CH_3$ | H | 3-$CH_3$ | $-CH(CH_3)-COOCH_3$ | b.p. 146°/5Torr |
| iso$C_3H_7$ | H | H | $-CH(CH_3)-COOCH_3$ | b.p. 110°/0.2Torr |
| iso$C_3H_7$ | iso$C_3H_7$ | H | $-CH(CH_3)-COOCH_3$ | b.p. 105°/0.5Torr |
| t . $C_4H_9$ | H | H | $-CH(CH_3)-COOCH_3$ | b.p. 93°/0.07Torr |
| $CH_3$ | H | 4-Cl | $-CH(CH_3)-COOCH_3$ | b.p. 125 – 127°/0.07Torr |
| $CH_3$ | Cl | H | $-CH(CH_3)-COOCH_3$ | b.p. 88 – 89°/0.03Torr |
| $CH_3$ | $CH_3$ | 4-Br | $-CH(CH_3)-COOCH_3$ | m.p. 31.5 – 32.5° |
| $CH_3$ | $CH_3$ | 3-Br | $-CH(CH_3)-COOCH_3$ | m.p. 46 – 47.5° |
| F | H | H | $-CH(CH_3)-COOCH_3$ | b.p. 98°/0.15Torr |
| Cl | H | H | $-CH(CH_3)-COOCH_3$ | b.p. 90 – 100°/0.09Torr |
| Br | H | H | $-CH(CH_3)-COOCH_3$ | b.p. 110°/0.01Torr |
| I | H | H | $-CH(CH_3)-COOCH_3$ | b.p. 105°/0.15Torr |
| $nC_4H_9O-$ | H | H | $-CH(CH_3)-COOCH_3$ | b.p. 132°/0.5Torr |
| $CH_3$ | H | 4-$CH_3O-$ | $-CH(CH_3)-COOCH_3$ | b.p. 131°/0.5Torr |
| $CH_3$ | H | 4sec.-$C_4H_9O-$ | $-CH(CH_3)-COOCH_3$ | b.p. 138°/0.15Torr |
| Cl | H | 5-Cl | $-CH(CH_3)-COOCH_3$ | m.p. 51.5 – 54° |
| $CH_3$ | $C_2H_5$ | H | $-CH(CH_3)-CONH_2$ | b.p. 155 – 157°/0.1Torr |
| $C_2H_5$ | $C_2H_5$ | H | $-CH(CH_3)-CONH_2$ | m.p. 71 – 73° |
| $C_2H_5$ | $C_2H_5$ | H | $-CH_2-CONH_2$ | m.p. 103 – 106° |
| $C_2H_5$ | $C_2H_5$ | H | $-CH_2-COOC_2H_5$ | b.p. 100 – 103°/0.04Torr |
| $C_2H_5$ | $C_2H_5$ | H | $-CH_2-CON(CH_3)_2$ | wax-like |
| $CH_3$ | $CH_3$ | H | $-CH_2-CONH_2$ | m.p. 89 – 91° |
| $CH_3$ | $CH_3$ | H | $-CH(CH_3)-CONH_2$ | m.p. 102 – 103° |
| $CH_3$ | $CH_3$ | H | $-CH(CH_3)-CONHCH_3$ | m.p. 75 – 76° |
| $CH_3$ | $CH_3$ | H | $-CH(CH_3)-CONCH_3$ <br> $\quad\quad\quad\quad\quad\quad\vert$ <br> $\quad\quad\quad\quad\quad\quad CH_3$ | b.p. 104 – 108°/0.02Torr |
| $C_2H_5$ | $C_2H_5$ | H | $-CH_2-CONHCH_3$ | m.p. 59 – 61.5° |
| $C_2H_5$ | $C_2H_5$ | H | $-CH_2-CONHC_2H_5$ | m.p. 79 – 80° |
| $CH_3$ | $CH_3$ | H | $-CH_2-COOCH_3$ | b.p. 155 – 160°/20Torr |
| $CH_3$ | Cl | H | $-CH(CH_3)-COOC_2H_5$ | b.p. 110 – 120°/0.3Torr |
| $CH_3$ | $C_2H_5$ | H | $-CH_2-COOCH_3$ | b.p. 168 – 171°/30Torr |
| $CH_3$ | Cl | H | $-CH(CH_3)-CONCH_3$ | m.p. 51 – 53° |

EXAMPLE 2

Manufacture of

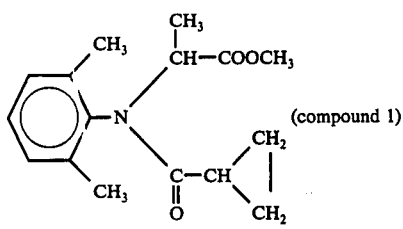

(compound 1)

N-(1'-methoxycarbonyl-ethyl)-N-cylopropylcarbonyl-2,6-dimethylaniline.

With stirring 51.8 g of α-(2,6-dimethylanilino)-propionic acid methyl ester in 200 ml of abs. toluene were treated at room temperature with 31.3 g of cyclopropanecarboxylic acid chloride in 50 ml of abs. toluene. After addition of 2 ml of dimethyl formamide the reaction mixture was refluxed for 2 hours and then the solvent and the excess cyclopropanecarboxylic acid chloride were distilled off in vacuo. The residual oil was crystallised by trituration with a small amount of petroleum ether. Compound 1 melted at 84°-87° C after recrystallisation in toluene/petroleum ether.

EXAMPLE 3

Manufacture of

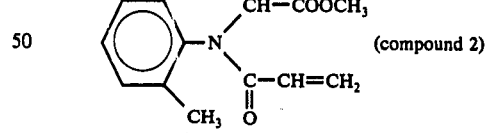

(compound 2)

N-(1'-methoxycarbonyl-ethyl)-N-vinylcarbonyl-2,6-dimethylaniline.

With good stirring, 80.6 g of acrylic acid chloride in 150 ml of abs. toluene were added dropwise at 20° C to 166 g of α-(2,6-dimethylanilino)-propionic acid methyl ester and 70.4 g of pyridine in 600 ml of abs. toluene. The reaction mixture was stirred for 20 hours and then precipitated pyridine hydrochloride was filtered off. The solvent was distilled off in vacuo and the residual oil fractionated in vacuo; b.p. 130°-135° C/0.01 Torr (compound 2).

The following compounds are manufactured in this manner or by one of the methods indicated hereinbefore ($R_1$ = 2-position):

Table I $$(R_5 = R_6 = H; X-R_3 = -\underset{\underset{CH_3}{|}}{CH}-COOCH_3)$$

| Comp. | $R_1$ | $R_2$ | $R_4$ | Physical constant (temperatures in °C) |
|---|---|---|---|---|
| 1 | $CH_3$ | 6-$CH_3$ | ◁ (cyclopropyl) | m.p. 84 – 87° |
| 2 | $CH_3$ | 6-$CH_3$ | $-CH=CH_2$ | b.p. 130 – 135°/0.01 Torr |
| 3 | $CH_3$ | 6-$CH_3$ | $-CH_2-CH(CH_3)_2$ | b.p. 140°/0.01 Torr |
| 4 | $CH_3$ | 4-Cl | $-C(CH_3)_3$ | |
| 5 | $CH_3$ | 6-$CH_3$ | $-C(CH_3)_3$ | m.p. 64 – 67° |
| 6 | $CH_3$ | H | $-C_6H_{13}(n)$ | |
| 7 | $CH_3$ | 6-$CH_3$ | $-CH_2SCN$ | m.p. 101 – 103° |
| 8 | $CH_3$ | 6-$C_2H_5$ | $-C(CH_3)_3$ | |
| 9 | Cl | 5-Cl | $-CH_2-CN$ | |
| 10 | $CH_3$ | 6-$CH_3$ | $-CH_3$ | b.p. 108 – 110°/0.03 Torr |
| 11 | $CH_3$ | 6-$CH_3$ | $-C_2H_5$ | m.p. 78 – 80° |
| 12 | $CH_3$ | 6-$CH_3$ | $-C_3H_7(n)$ | m.p. 49 – 51° |
| 13 | $CH_3$ | 6-$CH_3$ | $-C_3H_7(iso)$ | m.p. 122 – 123° |
| 14 | $CH_3$ | 6-$C_2H_5$ | $-C_3H_7(iso)$ | m.p. 93 – 95° |
| 15 | $CH_3$ | 6-$CH_3$ | $-C_6H_{13}(n)$ | b.p. 140 – 142°/0.05 Torr |
| 16 | $CH_3$ | 6-$CH_3$ | $-C_4H_9(iso)$ | b.p. 138 – 140°/0.03 Torr |
| 17 | $CH_3$ | 6-$CH_3$ | $-C_5H_{11}(n)$ | b.p. 140°/0.25 Torr |
| 18 | $CH_3$ | 3-$CH_3$ | $-C_3H_7(iso)$ | b.p. 133°/0.4 Torr |
| 19 | $CH_3$ | 3-$CH_3$ | $-CH(C_2H_5)-C_2H_5$ | b.p. 136 – 142°/0.03 Torr |
| 20 | $CH_3$ | 6-$CH_3$ | $-CH(C_2H_5)-C_2H_5$ | m.p. 71 – 72° |
| 21 | $CH_3$ | 6-Cl | $-CH_3$ | b.p. 123°/0.07 Torr |
| 22 | $CH_3$ | 6-Cl | $-C_3H_7(n)$ | b.p. 170°/0.04 Torr |
| 23 | $CH_3$ | 6-Cl | $-CH(C_2H_5)-C_2H_5$ | m.p. 70 – 71° |
| 24 | $CH_3$ | 6-$C_2H_5$ | $-CH(C_2H_5)-C_2H_5$ | b.p. 135 – 136°/0.1 Torr |
| 25 | $CH_3$ | 6-Cl | $-C_3H_7(iso)$ | m.p. 90 – 93° |
| 26 | $CH_3$ | 4-$CH_3-O-$ | $-C_3H_7(iso)$ | m.p. 96 – 98° |
| 27 | iso$C_3H_7$ | H | $-C_3H_7(iso)$ | m.p. 62 – 64° |
| 28 | iso$C_3H_7$ | H | $-CH(C_2H_5)-C_2H_5$ | m.p. 74 – 76° |
| 29 | n$C_4H_9-O-$ | H | $-C_3H_7(iso)$ | b.p. 152°/0.05 Torr |
| 30 | n$C_4H_9-O-$ | H | $-CH(C_2H_5)-C_2H_5$ | b.p. 145°/0.05 Torr |
| 31 | iso$C_3H_7$ | 6-iso$C_3H_7$ | $-C_3H_7(iso)$ | b.p. 133°/0.1 Torr |
| 32 | iso$C_3H_7$ | 6-iso$C_3H_7$ | $-CH(C_2H_5)-C_2H_5$ | b.p. 147°/0.03 Torr |
| 33 | iso$C_3H_7$ | 6-iso$C_3H_7$ | $-C_5H_{11}(n)$ | b.p. 143°/0.03 Torr |
| 34 | $CH_3$ | 4-$CH_3-O-$ | $-CH(C_2H_5)-C_2H_5$ | b.p. 154°/0.6 Torr |
| 35 | F | H | $-C_3H_7(iso)$ | b.p. 118 – 122°/0.35 Torr |
| 36 | F | H | $-C_4H_9(iso)$ | b.p. 105°/0.04 Torr |
| 37 | $CH_3$ | 6-$CH_3$ | $-CH=CH-CH_3$ | m.p. 80 – 82° |
| 38 | $CH_3$ | 6-$CH_3$ | $-CH=C(CH_3)_2$ | b.p. 118°/0.07 Torr |
| 39 | $CH_3$ | 6-$C_2H_5$ | $-CH=CH-CH_3$ | b.p. 130 – 132°/0.05 Torr |
| 40 | $CH_3$ | 6-$C_2H_5$ | $-CH=C(CH_3)_2$ | b.p. 128°/0.07 Torr |
| 41 | $C_2H_5$ | 6-$C_2H_5$ | $-CH=CH-CH_3$ | b.p. 136 – 138°/0.04 Torr |
| 42 | $C_2H_5$ | 6-$C_2H_5$ | $-CH=C(CH_3)_2$ | b.p. 135°/0.07 Torr |
| 43 | $CH_3$ | H | $-CH=CH_2$ | oil |
| 44 | $CH_3$ | H | $-CH=CH-CH_3$ | b.p. 130°/0.05 Torr |
| 45 | $CH_3-O-$ | H | $-CH=CH_2$ | b.p. 138 – 139°/0.02 Torr |
| 46 | $CH_3$ | 5-$CH_3$ | $-CH=CH-CH_3$ | b.p. 122 – 123°/0.05 Torr |
| 47 | $CH_3$ | 5-$CH_3$ | $-CH=C(CH_3)_2$ | b.p. 147°/0.09 Torr |
| 48 | $CH_3$ | 6-Cl | $-CH=C(CH_3)_2$ | b.p. 141°/0.03 Torr |
| 49 | $CH_3$ | 6-Cl | $-CH=CH-CH_3$ | m.p. 106 – 113° |
| 50 | $CH_3$ | 4-$CH_3$ | $-CH=C(CH_3)_2$ | b.p. 129 – 131°/0.03 Torr |
| 51 | iso$C_3H_7$ | H | $-CH=C(CH_3)_2$ | b.p. 129 – 131°/0.03 Torr |
| 52 | $CH_3$ | 6-$CH_3$ | $-CH_2-CH=CH_2$ | b.p. 143 – 145°/0.04 Torr |
| 53 | $CH_3$ | 4-$CH_3-O-$ | $-CH=C(CH_3)_2$ | b.p. 148 – 150°/0.1 Torr |
| 54 | iso$C_3H_7$ | H | $-CH=CH-CH_3$ | b.p. 142°/0.3 Torr |
| 55 | $CH_3$ | 3-$CH_3$ | $-CH=C(CH_3)_2$ | b.p. 147°/0.35 Torr |
| 56 | n$C_4H_9-O-$ | H | $-CH=C(CH_3)_2$ | b.p. 160°/0.05 Torr |

Table I-continued (R₅ = R₆ = H; X—R₃ = —CH(CH₃)—COOCH₃)

| Comp. | R₁ | R₂ | R₄ | Physical constant (temperatures in °C) |
|---|---|---|---|---|
| 57 | nC₄H₉—O— | H | —CH=CH—CH₃ | b.p. 157°/0.05 Torr |
| 58 | isoC₃H₇ | 6-isoC₃H₇ | —CH=CH—CH₃ | b.p. 140°/0.1 Torr |
| 59 | isoC₃H₇ | 6-isoC₃H₇ | —CH=C(CH₃)₂ | b.p. 170°/0.1 Torr |
| 60 | F | H | —CH=C(CH₃)₂ | b.p. 125°/0.3 Torr |
| 61 | F | H | —CH=CH—CH₃ | b.p. 126 – 131°/0.35 Torr |
| 62 | Cl | H | —CH=C(CH₃)₂ | b.p. 118 – 122°/0.05 Torr |
| 63 | Br | H | —CH=C(CH₃)₂ | b.p. 140°/0.04 Torr |
| 64 | Br | H | —CH=CH—CH₃ | b.p. 138°/0.04 Torr |
| 65 | Cl | H | —CH=CH—CH₃ | b.p. 132°/0.01 Torr |
| 66 | CH₃ | 6-Cl | cyclopropyl | b.p. 140 – 142°/0.04 Torr |
| 67 | CH₃ | 4-CH₃ | cyclopropyl | b.p. 138 – 140°/0.05 Torr |
| 68 | CH₃ | 5-CH₃ | cyclopropyl | b.p. 137 – 138°/0.07 Torr |
| 69 | C₂H₅ | 6-C₂H₅ | cyclopropyl | m.p. 43 – 45° |
| 70 | CH₃ | 6-C₂H₅ | cyclopropyl | m.p. 71 – 76° |
| 71 | CH₃ | 4-CH₃—O— | cyclopropyl | m.p. 82 – 83° |
| 72 | CH₃ | 3-CH₃ | cyclopropyl | b.p. 142°/0.03 Torr |
| 73 | CH₃ | 4-sec.-C₄H₉—O— | cyclopropyl | b.p. 156°/0.04 Torr |
| 74 | tert. C₄H₉ | H | cyclopropyl | b.p. 150 – 152°/0.1 Torr |
| 75 | nC₄H₉—O— | H | cyclopropyl | b.p. 149 – 151°/0.04 Torr |
| 76 | isoC₃H₇ | H | cyclopropyl | b.p. 135°/0.03 Torr |
| 77 | isoC₃H₇ | 6-iso-C₃H₇ | cyclopropyl | b.p 138°/0.03 Torr |
| 78 | F | H | cyclopropyl | b.p. 125°/0.03 Torr |
| 79 | Cl | H | cyclopropyl | b.p. 140°/0.06 Torr |
| 80 | I | H | cyclopropyl | b.p. 143°/0.15 Torr |
| 81 | CH₃ | 6-CH₃ | cyclobutyl | m.p. 92 – 96° |
| 82 | CH₃ | 6-CH₃ | cyclopentyl | m.p. 116 – 121° |
| 83 | CH₃ | 6-Cl | cyclopentyl | m.p. 105 – 108° |
| 84 | CH₃ | 6-CH₃ | cyclohexyl | m.p. 138 – 140° |
| 85 | CH₃ | 6-Cl | cyclohexyl | m.p. 129 – 130.5° |

Table I-continued $$(R_5 = R_6 = H; X-R_3 = -\overset{CH_3}{\underset{|}{CH}}-COOCH_3)$$

| Comp. | $R_1$ | $R_2$ | $R_4$ | Physical constant (temperatures in °C) |
|---|---|---|---|---|
| 86 | $CH_3$ | 6-$C_2H_5$ | cyclohexyl | m.p. 125 – 127° |
| 87 | $nC_4H_9$—O— | H | cyclohexyl | m.p. 73 – 74.5° |
| 88 | $CH_3$ | 3-$CH_3$ | cyclohexyl | m.p. 51 – 54° |
| 89 | $isoC_3H_7$ | H | cyclohexyl | b.p. 145°/0.04 Torr |
| 90 | tert. $C_4H_9$ | H | cyclohexyl | b.p. 152 – 155°/0.06 Torr |
| 91 | $CH_3$ | 4-$CH_3$ | cyclohexyl | m.p. 69 – 72° |
| 92 | $CH_3$ | 4-$CH_3$—O— | cyclohexyl | wax-like |
| 93 | F | H | cyclohexyl | b.p. 132°/0.05 Torr |
| 94 | Br | H | cyclohexyl | b.p. 135 – 145°/0.05 Torr |
| 95 | Cl | H | cyclohexyl | m.p. 102 – 104° |
| 96 | $CH_3$ | 4-$CH_3$ | —$CH_2$—SCN | m.p. 68 –72° |
| 97 | $CH_3$ | 5-$CH_3$ | —$CH_2$SCN | m.p. 86 – 88° |

Table II ($R_5 = R_6 = H$)

| Comp. | $R_1$ | $R_2$ | —X—$R_3$ | $R_4$ | Physical constant (temperatures in °C) |
|---|---|---|---|---|---|
| 98 | $CH_3$ | 6-$CH_3$ | —CH—$CONH_2$ <br> \| <br> $CH_3$ | cyclopropyl | m.p. 142.5-144° |
| 99 | $CH_3$ | 6-$CH_3$ | —CH—$CONH_2$ <br> \| <br> $CH_3$ | —$C(CH_3)_3$ | m.p. 175-177° |
| 100 | $C_2H_5$ | 6-$C_2H_5$ | —$CH_2$—$CONH_2$ | cyclopropyl | m.p. 140.5-143° |

Table II-continued ($R_5 = R_4 = H$)

| Comp. | $R_1$ | $R_2$ | $-X-R_3$ | $R_4$ | Physical constant (temperatures in °C) |
|---|---|---|---|---|---|
| 101 | $CH_3$ | 6-$CH_3$ | $-CH(CH_3)-CON(CH_3)_2$ | $-CH=C(CH_3)_2$ | b.p. 115–120° / 0.08 Torr |
| 102 | $CH_3$ | 6-$CH_3$ | $-CH(CH_3)-CONHCH_3$ | $-CH=CH-CH_3$ | m.p. 114–115° |
| 103 | $CH_3$ | 6-$CH_3$ | $-CH(CH_3)-CONHCH_3$ | cyclopropyl | m.p. 131–134° |
| 104 | $CH_3$ | 6-$CH_3$ | $-CH(CH_3)-CONH_2$ | $-CH=CH-CH_3$ | m.p. 149–150° |
| 105 | $CH_3$ | 6-Cl | $-CH(CH_3)-COOC_2H_5$ | $-CH=C(CH_3)_2$ | b.p. 146–150° |
| 106 | $CH_3$ | 6-Cl | $-CH(CH_3)-COOC_2H_5$ | $-CH=CH-CH_3$ | m.p. 88–92° |
| 107 | $C_2H_5$ | 6-$C_2H_5$ | $-CH_2-COOCH_3$ | $-CH=CH-CH_3$ | m.p. 55–57° |
| 108 | $C_2H_5$ | 6-$C_2H_5$ | $-CH_2-COOCH_3$ | $-C(CH_3)_3$ | m.p. 72.5–73° |
| 109 | $C_2H_5$ | 6-$C_2H_5$ | $-CH(CH_3)-CONH_2$ | $-CH_3$ | m.p. 141–142° |
| 110 | $C_2H_5$ | 6-$C_2H_5$ | $-CH_2-CONHCH_3$ | $-CH_3$ | m.p. 123–124° |
| 111 | $C_2H_5$ | 6-$C_2H_5$ | $-CH_2-CONHCH_3$ | $-C(CH_3)_3$ | m.p. 183–184° |
| 112 | $C_2H_5$ | 6-$C_2H_5$ | $-CH_2-CON(CH_3)_2$ | cyclopropyl | m.p. 71–74° |
| 113 | $C_2H_5$ | 6-$C_2H_5$ | $-CH_2-CON(CH_3)_2$ | cyclohexyl (H) | $n_D^{20}$ 1.6859 |
| 114 | $C_2H_5$ | 6-$C_2H_5$ | $-CH_2-CON(CH_3)_2$ | $-CH_3$ | m.p. 137–139° |
| 115 | $C_2H_5$ | 6-$C_2H_5$ | $-CH_2-COOCH_3$ | cyclopropyl | b.p. 132–134° /0.03 Torr |
| 116 | $C_2H_5$ | 6-$C_2H_5$ | $-CH_2-COOCH_3$ | $-C_3H_7(n)$ | b.p. 167–170° /0.4 Torr |
| 117 | $C_2H_5$ | 6-$C_2H_5$ | $-CH_2-COOCH_3$ | $-CH_3$ | b.p. 170° /0.5 Torr |
| 118 | $CH_3$ | 6-$CH_3$ | $-CH_2-CONHCH_3$ | $-CH_3$ | m.p. 129–130° |
| 119 | $CH_3$ | 6-$CH_3$ | $-CH_2-CONHCH_3$ | $-C_3H_7(n)$ | m.p. 63–65° |
| 120 | $C_2H_5$ | 6-$C_2H_5$ | $-CH_2CONH_2$ | $-CH_3$ | m.p. 138° |
| 121 | $CH_3$ | 6-$CH_3$ | $-CH_2-COOCH_3$ | $-CH_2-CH(CH_3)_2$ | b.p. 130° /0.01 Torr |
| 122 | $CH_3$ | 6-$CH_3$ | $-CH_2-CONHCH_3$ | $-CH_2-CH(CH_3)_2$ | m.p. 80–86° |
| 123 | $C_2H_5$ | 6-$C_2H_5$ | $-CH_2-CONHCH_3$ | $-CH=CH-CH_3$ | m.p. 107–109° |
| 124 | $C_2H_5$ | 6-$C_2H_5$ | $-CH_2-CONH_2$ | $-C_3H_7(n)$ | m.p. 103° |
| 125 | $C_2H_5$ | 6-$C_2H_5$ | $-CH_2-CONHC_2H_5$ | $-CH_3$ | m.p. 73–74° |
| 126 | $C_2H_5$ | 6-$C_2H_5$ | $-CH_2-CONHC_2H_5$ | $-C_4H_9(iso)$ | b.p. 152° /0.01 Torr |

Table II ($R_5$ 3-position; $R_2$ 6-position; $X-R_3 = -CH(CH_3)-COOCH_3$)

| Comp. | $R_1$ | $R_2$ | $R_5$ | $R_6$ | $R_4$ | Physical constant (temperatures in °C) |
|---|---|---|---|---|---|---|
| 127 | $CH_3$ | $CH_3$ | H | 4-$CH_3$ | $-C_3H_7(n)$ | m.p. 65–66.5° |
| 128 | $C_2H_5$ | $CH_3$ | $CH_3$ | H | $-CH=CH-CH_3$ | b.p. 150–152° /0.06 Torr |
| 129 | $C_2H_5$ | $CH_3$ | $CH_3$ | H | $-C_3H_7(n)$ | b.p. 143–145° /0.03 Torr |
| 130 | $CH_3$ | $CH_3$ | $CH_3$ | H | $-CH=CH-CH_3$ | b.p. 138–140° /0.1 Torr |
| 131 | $CH_3$ | $CH_3$ | $CH_3$ | H | $-C_3H_7(n)$ | b.p. 130–132° /0.04 Torr |
| 132 | $CH_3$ | $CH_3$ | $CH_3$ | H | cyclopropyl | b.p. 130–132° /0.04 Torr |
| 133 | $CH_3$ | $CH_3$ | Br | H | $-CH=CH-CH_3$ | b.p. 155–160° |
| 134 | $CH_3$ | $C_2H_5$ | $CH_3$ | H | $-C_3H_7(n)$ | |
| 135 | $CH_3$ | $CH_3$ | H | 4-$CH_3$ | $-CH_2-CH(CH_3)_2$ | |
| 136 | $CH_3$ | $CH_3$ | $CH_3$ | H | $-CH_2-CH(CH_3)_2$ | |
| 137 | $CH_3$ | $CH_3$ | $CH_3$ | 5-$CH_3$ | $-CH_2-CH(CH_3)_2$ | |
| 138 | $CH_3$ | $CH_3$ | $CH_3$ | 5-$CH_3$ | $-C_3H_7(n)$ | b.p. 174–177° /0.04 Torr |
| 139 | $CH_3$ | $CH_3$ | $CH_3$ | 5-$CH_3$ | $-CH=CH-CH_3$ | b.p. 184–189° /0.03 Torr |
| 140 | $CH_3$ | $CH_3$ | $CH_3$ | 5-$CH_3$ | cyclopropyl | |
| 141 | $CH_3$ | $C_2H_5$ | $CH_3$ | H | $-CH=CH-CH_3$ | b.p. 128–129° /0.03 Torr |
| 142 | $CH_3$ | $CH_3$ | H | 4-$CH_3$ | $-CH=CH-CH_3$ | b.p. 138–140° /0.1 Torr |
| 143 | $CH_3$ | $CH_3$ | H | 4-$CH_3$ | cyclopropyl | m.p. 88.5–89.5° |
| 144 | $CH_3$ | $CH_3$ | H | 4-Cl | $-C_3H_7(n)$ | b.p. 147–149° /0.03 Torr |

Table II-continued (R$_5$ 3-position; R$_2$ 6-position; X—R$_3$ = —CH(CH$_3$)—COOCH$_3$)

| Comp. | R$_1$ | R$_2$ | R$_5$ | R$_6$ | R$_4$ | Physical constant (temperatures in ° C) |
|---|---|---|---|---|---|---|
| 145 | CH$_3$ | Cl | H | 4-Cl | cyclopropyl | b.p. 162–165° /0.02 Torr |
| 146 | CH$_3$ | CH$_3$ | H | 4-Br | cyclopropyl | m.p. 122–123.5° |
| 147 | CH$_3$ | CH$_3$ | H | 4-Cl | —CH=CH—CH$_3$ | b.p. 152–154° /0.04 Torr |
| 148 | CH$_3$ | CH$_3$ | H | 4-CH$_3$ | —CH$_2$—CH=CH$_2$ | |
| 149 | CH$_3$ | CH$_3$ | CH$_3$ | H | —CH$_2$—CH=CH$_2$ | |
| 150 | CH$_3$ | CH$_3$ | H | 4-Cl | cyclopropyl | b.p. 172–174° /0.02 Torr |
| 151 | CH$_3$ | CH$_3$ | H | 4-Br | —CH=CH—CH$_3$ | m.p. 110–112° |
| 152 | CH$_3$ | CH$_3$ | H | 4-Br | —C$_3$H$_7$(n) | m.p. 102–105° |
| 153 | CH$_3$ | Cl | H | 4-Cl | —C$_3$H$_7$(n) | b.p. 189–193° /0.02 Torr |
| 154 | CH$_3$ | Cl | H | 4-Br | cyclopropyl | |
| 155 | CH$_3$ | Cl | H | 4-Br | —C$_3$H$_7$(n) | b.p. 187–190° /0.03 Torr |
| 156 | CH$_3$ | Cl | H | 4-Cl | —CH=CH—CH$_3$ | b.p. 187–190° 0.01 Torr |
| 157 | CH$_3$ | Cl | H | 4-Br | —CH=CH—CH$_3$ | b.p. 193–195° /0.02 Torr |

The compounds of the formula I can be used with other suitable pesticides or active substances that promote plant growth in order to widen their activity spectrum. The compounds of the formula I can be used by themselves or together with suitable carriers and/or other additives. Suitable carriers and additives can be solid or liquid and correspond to the customary substances used in formulation technology, for example natural or regenerated mineral substances, solvents, dispersants, wetting agents, stickers, thickeners, binders or fertilisers. The amount of active substance in commercially useful compostions is between 0.1 and 90%.

The compounds of the formula I can be applied in the following process forms (the percentages by weight in brackets denote the advantageous amounts of active substance):

Solid forms: dusts and tracking agents (up to 10%); granules; coated granules impregnated granules and homogeneous granules (1 to 80%);

liquid forms:
(a) active substance concentrates which are dispersible in water: wettable powders and pastes (25–90% in the commercial pack, 0.01 to 15% in ready for use solution); emulsion concentrates and concentrated solutions (10 to 50%; 0.01 to 15% as ready for use solution);
(b) solutions (0.1 to 20%).

The active substances of the formula I can be formulated, for example, as follows:

Dusts: The following substances are used to manufacture (a) 50% and (b) a 2% dust:

(a)

5 parts of active substance
95 parts of talcum;

(b)

2 parts of active substance
1 part of highly disperse silicic acid
97 parts of talcum.

The active substances are mixed with the carriers and ground and in this form can be processed to dusts for application.

Granules: The following substances are used to manufacture 5% granules:

5 parts of active substance
0.25 part of epichlorohydrin
0.25 part of cetyl polyglycol ether
3.50 parts of polyethylene glycol
91 parts of kaolin (particle size 0.3 – 0.8 mm).

The active substance is mixed with epichlorohydrin and the mixture is dissolved in 6 parts of acetone. Then polyethylene glycol and cetyl polyglycol ether are added. The resultant solution is sprayed on kaolin and the acetone is evaporated in vacuo. Such microgranules are advantageously used for combating soil fungi.

Wettable powders: The following constituents are used to manufacture (a) a 70%, (b) a 40%, (c) and (d) a 25% and (c) a 10% wettable powder:

(a)

70 parts of active substance
5 parts of sodium dibutyl naphthylsulphonate
3 parts of naphthalenesulphonic acid/phenolsulphonic acid/formaldehyde condensate (3:2:1)
10 parts of kaolin
12 parts of Champagne chalk (b)

40 parts of active substance
5 parts of sodium lignin sulphonate
1 part of sodium dibutylnaphthalenesulphonic acid
54 parts of silicic acid (c)

25 parts of active substance
4.5 parts of calcium lignin sulphonate
1.9 parts of a Champagne chalk/hydroxyethyl cellulose mixture (1:1)
1.5 parts of sodium dibutylnaphthalenesulphonate
19.5 parts of silicic acid
19.5 parts of Champagne chalk
28.1 parts of kaolin (d)

25 parts of active substance 2.5 parts of isooctylphenoxy-polyethylene-ethanol
1.7 parts of a Champagne chalk/hydroxyethyl cellulose mixture (1:1)
8.3 parts of sodium aluminium silicate
16.3 parts of kieselguhr
46 parts of kaolin (e)

10 parts of active substance
3 parts of a mixture of the sodium salts of saturated fatty alcohol sulphates
5 parts of naphthalenesulphonic acid/formaldehyde condensate
82 parts of kaolin.

The active substances are intimately mixed in suitable mixers with the additives and ground in appropriate mills and roolers. Wettable powders of excellent wettability and suspension powder are obtained. These wettable powders can be diluted with water to give suspensions of every desired concentration and can be used in particular for application to leaves.

Emulsifiable concentrates: The following substances are used to manufacture a 25% emulsifiable concentrate:

25 parts of active substance
2.5 parts of epoxidised vegetable oil
10 parts of an alkylarylsulphonate/fatty alcohol polyglycol ether mixture
5 parts of dimethyl formamide
57.5 parts of xylene.

By diluting such concentrates with water it is possible to manufacture emulsions of every desired concentration which are especially suitable for application to leaves.

EXAMPLE 4

Action against *Phytophthora infestans* on *Solanum lycopersicum* (tomatoes)

(Ia) Residual preventive action

Solanum lycopersicum plants of the "Roter Gnom" variety are infected when 3 weeks old with a zoospore suspension of Phytophthora infestans after they have been sprayed with a broth prepared from the active substance processed to a wettable powder and containing 0.06% of active substance, and dried. They are then kept for 6 days in a climatic chamber at 18° to 20° and high humidity, which is produced with an artificial wet fog. After this time typical leaf specks appear. Their number and size are the criterion for evaluating the tested substance.

Application of e.g. compounds nos. 1, 2, 7, 12, 37, 39, 49 and 66 resulted in the fungal attack being kept under 20%.

(1b) Curative action

"Roter Gnom" tomato plants are sprayed when 3 weeks old with a zoospore suspension of the fungus and incubated in a climatic chamber at 18° to 20° C and saturated humidity. The humidifying is interrupted after 24 hours. After the plants have been dried, they are sprayed with a broth which contains the active substance formulated as wettable powder in a concentration of 0.06%. After the spray coating has dried, the plants are again kept in the humid chamber for 4 days. Size and number of the typical leaf specks which have occured during this time are the criterion for evaluating the effectiveness of the tested substances.

Application of e.g. compounds nos. 1, 2, 7, 12, 23, 37, 39, 46, 49, 66, 121, 132 and 158 reduced the fungal attack to less than 20%.

The compounds of Examples I, II and III as well as compounds nos. 3, 5, 7, 9, 11, 12, 15 and 17 of Table 1 of U.S. Pat. No. 3,598,859 were inactive in this test.

(II) Preventive-systemic action

The active substance is applied as wettable powder in a concentration of 0.006% (referred to the volume of the soil) to the surface of the soil of 3 weeks old "Roter Gnom" tomatoes in pots. Three days later the underside of the leaves of the plants are sprayed with a zoospore suspension of Phytophthora infestans. The plants are then kept for 5 days in a spray chamber at 18° to 20° C and saturated humidity, after which time typical leaf specks form. The size and number of the specks serve as criterion for evaluating the effectiveness of the tested substance.

Application of e.g. compounds nos. 1, 2, 7, 11, 12, 22, 23, 25, 37, 39, 40, 49, 66, 79, 130, 131, 132, 133 and 141 kept the fungal attack under 20%.

EXAMPLE 5

Action against *Plasmopara viticola* (Bert. et Curt.) (Berl. et de Toni) on vines (a) Residual preventive action Vine cuttings of the variety "Chasselas" were reared in a greenhouse. Three plants in the 10 leaf stage were sprayed with a broth (0.02% active substance) prepared from the active substance and formulated as a wettable powder. After the coating layer had dried, the plants were infected on the underside of the leaves with the spore suspension of the fungus. The plants were subsequently kept for 8 days in a humid chamber, after which time symptoms of the disease were visible on the control plants. The number and size of the infected areas on the treated plants served as criterion for evaluating the effectiveness of the tested active substances.

Application e.g. of compounds nos. 1, 7, 12, 22, 25, 37, 49, 66, 91, 101, 102, 103, 119, 120, 121, 125, 127, 130, 131, 132, 133 and 142 kept the fungal attack to below 20%.

The compounds of Examples I, II and III as well as compounds nos. 3, 5, 7, 9, 11, 12, 15 and 17 of Table 1 of U.S. Pat. No. 3,598,859 were inactive in this test.

(b) Curative action

Vine cuttings of the variety "Chasselas" were reared in a greenhouse and infected in the 10 leaf stage with a spore suspension of Plasmopara viticola on the underside of the leaves. After they had been kept for 24 hours in a humid chamber, the plants were sprayed with an active substance broth (0.02% active substance) prepared from a wettable powder of the active substance.

The plants were then kept for a further 7 days in a humid chamber, after which time the symptoms of the disease were visible on the control plants. The size and number of the infected areas served as criterion for evaluating the effectiveness of the tested substances.

Application e.g. of compounds nos. 1, 7, 12, 37, 39, 49, 66, 71, 126, 127, 130, 131, 132 and 133 reduced the fungal attack to less than 20%.

EXAMPLE 6

Action against *Erysiphe graminis* on *Hordeum vulgare* (barley) Residual protective action Barley plants c. 8 cm in height were sprayed with a spray broth (0.02% active substance) prepared from a wettable powder of the active substance. After 48 hours the treated plants were dusted with conidia of the fungus. The infected barley plants were stood in a greenhouse at c. 22° C and the fungus infection was evaluated after 10 days.

Application of compounds nos. 33, 34, 56, 57, 58, 73 and 74 kept the fungal attack below 20%.

I claim:

1. A compound of the formula Ia

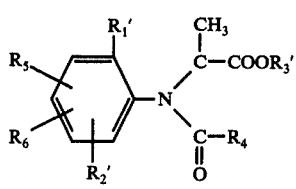

wherein
$R_1'$ represents methyl
$R_2'$ represents methyl, ethyl or chlorine
$R_5$ represents hydrogen, alkyl of 1 to 3 carbon atoms or halogen and
$R_6$ represents hydrogen or methyl; the total number of carbon atoms in $R_1'$, $R_2'$, $R_5$, $R_6$ not exceeding 4;
$R_3'$ represents methyl and
$R_4$ represents alkyl of 2 to 4 carbon atoms, alkenyl of 2 to 4 carbon atoms or cycloalkyl of 3 to 4 carbon atoms.

2. A compound as claimed in claim 1 wherein
$R_2$ represents methyl,
$R_5$ represents hydrogen, methyl, chlorine or bromine,
$R_6$ represents hydrogen and
$R_4$ represents vinyl, allyl, n-propyl or cyclopropyl.

3. A compound as claimed in claim 1 wherein
$R_2$ represents chlorine or ethyl,
$R_5$ and $R_6$ represent hydrogen and
$R_4$ represents vinyl, allyl, n-propyl or cyclopropyl.

4. A compound according to claim 2 which is N-(1'-methoxycarbonyl-ethyl)-N-crotonoyl-3-bromo-2,6-dimethylaniline of the formula

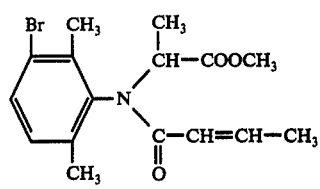

5. A compound according to claim 2 which is N-(1'-methoxycarbonyl)-N-n-butyryl-2,3,6-trimethylaniline of the formula

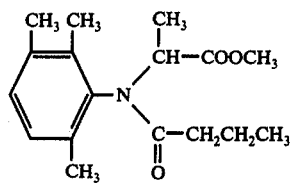

6. A compound according to claim 2 which is N-(1'-methoxycarbonyl)-N-cyclopropanoyl-2,3,6-trimethylaniline of the formula

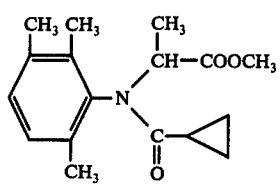

7. N-(1'-methoxycarbonyl-ethyl)-N-cyclopropanoyl-2-methyl-4-sec.butoxy-aniline of the formula

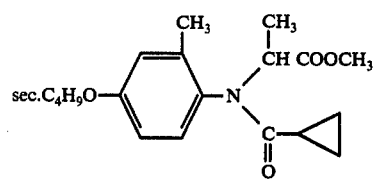

8. The D-configuration of the compounds of claim 1.

9. A microbicidal composition containing as active substance an effective amount of a compound as claimed in claim 1, together with a suitable carrier therefor.

10. A microbicidal composition containing as active substance an effective amount of a compound as claimed in claim 2, together with a suitable carrier therefor.

11. A microbicidal composition containing as active substance an effective amount of a compound as claimed in claim 3, together with a suitable carrier therefor.

12. A microbicidal composition containing as active substance an effective amount of a compound as claimed in claim 4, together with a suitable carrier therefor.

13. A microbicidal composition containing as active substance an effective amount of a compound as claimed in claim 5, together with a suitable carrier therefor.

14. A microbicidal composition containing as active substance an effective amount of a compound as claimed in claim 6, together with a suitable carrier therefor.

15. A microbicidal composition containing as active substance an effective amount of a compound as claimed in claim 7, together with a suitable carrier therefor.

16. A microbicidal composition containing as active substance an effective amount of a compound as claimed in claim 8, together with a suitable carrier therefor.